United States Patent [19]

Tresouthick et al.

[11] Patent Number: 4,993,838
[45] Date of Patent: Feb. 19, 1991

[54] DUST MONITOR

[75] Inventors: Stewart W. Tresouthick, Arlington Heights; Hugh Love, Green Oaks, both of Ill.

[73] Assignee: Construction Technology Laboratories, Inc., Skokie, Ill.

[21] Appl. No.: 208,383

[22] Filed: Jun. 17, 1988

[51] Int. Cl.$^5$ ............................................. G01N 21/59
[52] U.S. Cl. .................................................... 356/439
[58] Field of Search ........................... 356/36, 438, 439

[56] References Cited

U.S. PATENT DOCUMENTS

| | | | |
|---|---|---|---|
| 2,822,719 | 2/1958 | Fike | 356/438 |
| 3,867,640 | 2/1975 | Paulsen | 250/573 |
| 4,021,713 | 5/1977 | Suga | 250/574 |
| 4,506,541 | 3/1985 | Cunningham | 250/308 |

Primary Examiner—Richard A. Rosenberger
Attorney, Agent, or Firm—Michael D. Rechtin; Philip P. Mann

[57] ABSTRACT

An apparatus and method for reliably generating simulations of actual dust suspension conditions and measuring the associated density of suspended dust. The dust monitor is constructed to permit generation of dust suspensions by achieving various pre-selected motions for the test material, such as a rolling motion or swirling motion relative to the forward direction of travel of the test material. The apparatus and method permit prediction and control of the propensity to form dust suspensions during actual operating situations in the field.

18 Claims, 1 Drawing Sheet

DUST MONITOR

BACKGROUND OF THE INVENTION

This invention is concerned generally with an apparatus and a method for measuring suspended dust particle density and more particularly is concerned with an apparatus and method for reliably generating simulations of actual dust suspension conditions and measuring the associated density of suspended dust.

With the advent of rigorous environmental laws there has been an increased need to accurately predict and to characterize dust suspensions. The concept of measuring dust suspension conditions is generally known in the art. Prior art references show that dust particles can be suspended in air and monitored by dropping or blowing powder materials into a chamber wherein photoelectric sensors measure the magnitude of light intensity transmitted through a path length of suspended dust particles. However, the ability to accurately predict and to characterize dust suspensions in real systems involves the proper generation of the dust suspension. In the prior art there has been little or no effort concerned with generating dust suspension conditions which provide good correlation to results in real systems. Rather, the prior art tends to be simplistic and generates suspensions by simply dropping dust into a tray (see U.S. Pat. No. 2,822,719). Alternatively, the prior art follows a brute force method of installing a photosensor device within an actual operating system having dust suspensions associated therewith (see, U.S. Pat. No. 3,867,640). Such apparatus and methods are insufficient to achieve accurate simulations of any meaningful variety of actual dust suspension conditions and thus do not provide a sound fundamental approach for predicting and characterizing the dustiness present under various real operating conditions.

BRIEF SUMMARY OF THE INVENTION

It is therefore an object of the invention to provide an improved apparatus and method for producing dust suspensions in an atmosphere.

It is another object of the invention to provide a novel apparatus and method for generating and characterizing accurate simulations of dust suspension conditions in real systems.

It is a further object of the invention to provide an improved apparatus and method for varying physical and/or chemical parameters associated with a material while characterizing the propensity of the material mixture to form a dust suspension.

It is an additional object of the invention to provide a novel apparatus and method for the manufacture of materials having optimized characteristics for reducing the propensity to dustiness.

In one aspect of the invention, the apparatus is used to generate an accurate simulation of a powder material's propensity to dust under real operating conditions. These operating conditions can include the manufacture of materials (such as a powder material) or the transport of the material into and out of storage facilities. The apparatus includes a source to supply material for the test of dustiness and a container in communication with the material source for receiving the material. The container includes a structure for diverting the material flow to achieve a preselected motion which provides a dust suspension indicative of actual conditions of interest in the field. The ability to simulate actual dust suspension conditions of interest enables accurate prediction of propensity to dust of a material and even allows changes to be implemented in the manufacture of the material to achieve the desired result.

Further objects and advantages of the present invention, together with the organization and manner of operation thereof, will become apparent from the following detailed description of the invention when taken in conjunction with the accompanying drawings wherein like reference numerals designate like features throughout the several views.

DETAILED DESCRIPTION OF PREFERRED EMBODIMENTS

Figure 1:
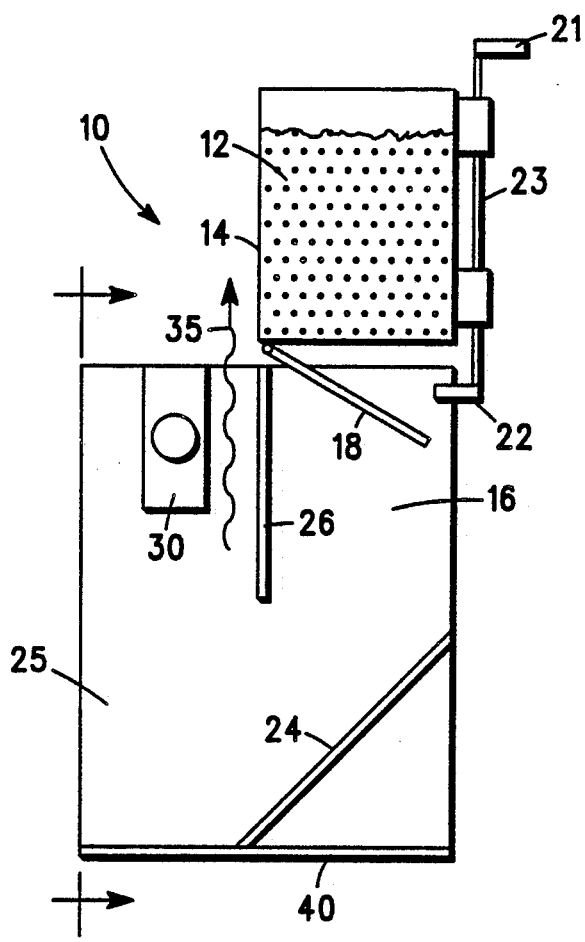
FIG. 1 is a front elevation view of one embodiment of the apparatus of the invention.
Figure 2:
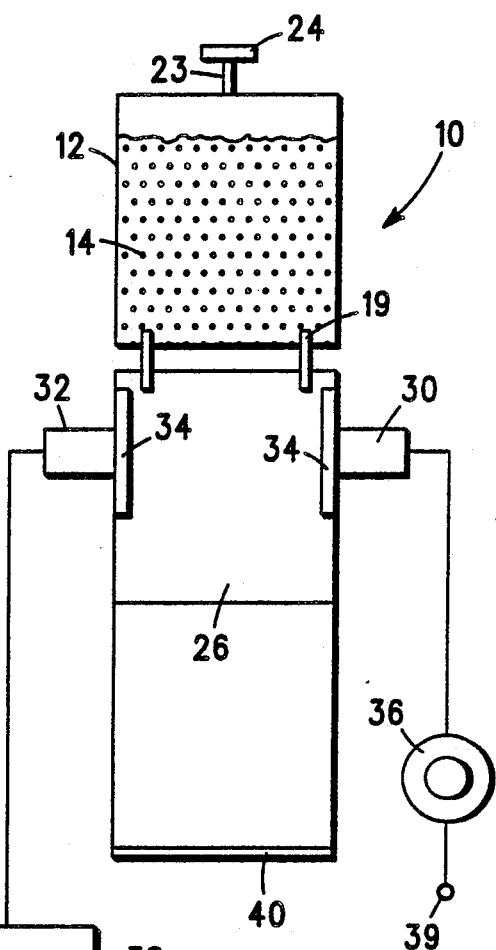
FIG. 2 is a side elevation view of the apparatus taken along line 2—2 in FIG. 1.
Figure 3:
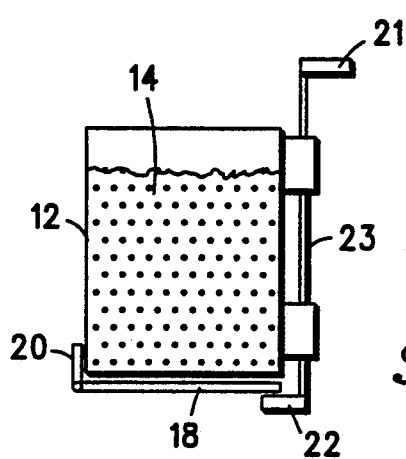
FIG. 3 is an end view of a reservoir for holding the powder material to be tested.

In FIGS. 1–3 is illustrated one form of an apparatus 10 for generating a dust suspension from a material (such as a powder material) and measuring characteristics thereof, particularly the propensity to form a dust suspended in an atmosphere. The apparatus includes means for supplying a material, such as a reservoir 12, shown in FIGS. 1 and 2 holding a powder material 14. The powder material 14 is placed in the reservoir 12 and if desired, the user can remove the reservoir 12 to a vibration device (not shown) to compact the powder material 14 to achieve selected starting conditions. Other suitable supply means for the powder material 14 can include any device in communication with the apparatus 10 and able to move the powder material 14 into a container means, such as a diversion chamber portion 16. The diversion chamber portion 16 is used to achieve a preselected motion for the powder material 14. The reservoir 12 can be separately disposed from and removable by the user from the diversion chamber portion 16 with index pins 19 aligning these two structures. The reservoir 12 has a free swinging door 18 constituting the bottom portion thereof. Hinges 20 and latch 22 are arranged such that the bottom of the reservoir 12 is smooth and uninterrupted. The latch 22 allows the door 18 to be opened rapidly by using a mechanical knob 21 operatively connected to the latch 22 by a rod 23.

When the free swinging door 18 is opened, the powder material 14 undergoing test moves by falling into the diversion chamber portion 16. The desired preselected motion for the powder material is achieved in the illustrated embodiment by interposing an inclined ramp 24 shown n FIG. 1. When the powder material 14 impacts the interposed inclined ramp 24, a rolling, upward motion is achieved generally along direction 35 relative to the direction of forward travel of the powder material 14. As the powder material 14 rapidly discharges from the reservoir 12, it displaces air before it. This displacement of the air increases the velocity of the air and entrains a size range of the powder material 14 in the air. This upward travel is also adjustable by having a variable size opening (not shown) to the atmosphere in selected portions of the walls of the apparatus 10. The inclined ramp 24 therefore achieves the desired, preselected motion for the powder material 14, enabling the imitation of actual operating conditions which create dust suspensions in the field. Other geometries can be used for achieving other preselected motions, such as a spiral ramp (not shown) to induce swirling action relative to the direction of forward travel for the powder material 14. The inclined ramp 24 can also be adjusted to various angles between zero degrees and ninety degrees to achieve the preselected motion of interest. In the case of the powder material 14 being a well-known construction grade cement, the angle of the inclined ramp 24 is preferably between about forty-five degrees to seventy degrees.

After the moving powder material 14 strikes the inclined ramp 24, the powder material 14 travels into a measurement chamber portion 25 separated by a baffle 26 from the diversion chamber portion 16 of the apparatus 10. The powder material 14 moves upwardly through the chamber portion 25 and out the open top (not shown) of the chamber portion 25 to the atmosphere. The dimensions of the walls of the two chamber portions 16 and 25, and the dimensions of the baffle 26 allow control primarily of the velocity of the moving powder material 14. For example, when performing measurements on construction grade cement powders, optimum correlation was obtained with field conditions when the ratios of side wall dimensions of the diversion chamber portion 16 and the measurement chamber portion 25 ranged from 1:1 to 1:1.5, while the ratio of the height of the baffle 26 to the height of the chamber portions is preferably about 1:1.5 to 1:2.5. The most preferred ratio of the sides of the diversion chamber portion 16 is 1:1.3, while for the sides of the measurement chamber portion 25 the ratio is 1:1.1; and the ratio of the baffle height to chamber portions is 1:2.

Once the desired suspension has been achieved, the dust density is measured using a light source 30 and a photosensor 32 shown in FIGS. 1 and 2. This general method of measuring dust densities is a conventional one (see, for example, U.S. Pat. No. 4,021,713 which is incorporated by reference herein). These means for measuring dustiness in FIGS. 1 and 2 are adjustable laterally and vertically in a conventional mechanical manner to enable further freedom in optimizing the correlation between the simulated dust conditions in the apparatus 10 and actual field conditions of dustiness. The light source 30 and the photosensor 32 are generally disposed opposite one another, and each are protected from dust accumulation by a glass plate 34. The light source 30 can be any stable source, such as a long life quartz lamp. The photosensor 32 is selected for compatibility with the light source 30 which can have adjustable intensity by virtue of a potentiometer or rheostat 36 connected between a power supply 39 and the light source 30. In a conventional manner the output of the photosensor 32 can be selected to be in millivolts or milliamperes. The output can then be displayed on a plotter 38 or other suitable data output and collection device.

Calibration of photosensor measurements for purposes of determining propensity to form suspended dust can be done using any conventional optical standard, such as the Ringleman method (opacity test of a dust suspension). The Ringleman method can be used to establish a base line, and relative increases or decreases below the base line establish a Ringleman number for an unknown dust suspension.

Data can also be collected and quantified in the illustrated embodiment by measuring the initial peak height of the light transmitted through the dust suspension and also determine the average transmissivity for 25%, 50% and 75% of the selected test time. The initial peak height can also be correlated to selected standard methods of measure in the field, such as the Ringleman test. The adjustable nature of the relative position of the light source 30 and the photosensor 32, the plotter 38 drive speed, the light intensity and the geometry of the apparatus 10 allow optimum correlation with actual results in the field. Furthermore, in a known manner the average of data taken at three different time intervals can be related to the tendency of the powder material 14 to remain airborne.

After completion of the measurements on the powder material 14, the apparatus 10 can be opened by removal of a bottom plate 40 affixed to the apparatus 10 by typical fasteners, such as bolts and screws (not shown). This construction allows the user to clean the interior walls of the two chamber portions 16 and 25 and the baffle 26.

The apparatus 10 therefore allows measurement of the propensity to form dust suspensions without having to rely on full scale field tests of operating systems. This enables prediction of potential of dust formation difficulties which the user can compensate for in the field using appropriate precautions. The user can also choose to alter manufacturing, storage or material handling parameters (chemical and/or mechanical and/or physical) of the powder material 14 and starting raw material to avoid a propensity to form excessively dusty suspensions. The apparatus 10 is not limited to performing measurements on powdered material but can involve a mixture of powder and larger sizes of materials and even mixtures of solids and liquids which are often encountered in industry.

While preferred embodiments of the present invention have been illustrated and described, it will be understood that changes and modification can be made therein without departing from the invention in its broader aspects. Various features of the invention are defined in the following claims.

What is claimed is:

1. An apparatus for generating a dust suspension of powder material and for measuring dustiness characteristics of said powder material dust suspension, comprising:

means for supplying a material including at least said powder material;

container means for receiving said material movable from said means for supplying, said container means including an inclined ramp surface for achieving a pre-selected motion for said material moved from said means for supplying into said container means and said container means further including a downstream opening allowing said moving material to pass out of said container means; and means coupled to said container means for measuring said dustiness characteristics of said powder material.

2. The apparatus as defined in claim 1 wherein said dustiness characteristics of said powder material comprise at least one of density of said powder material dust suspension, particle size distribution of said powder material suspension and motion parameters of said moved material.

3. The apparatus as defined in claim 1 wherein said means for measuring comprises a photoelectric sensor device.

4. The apparatus as defined in claim 1 further including means for controlling the packing density of said powder material in said means for supplying.

5. An apparatus for generating a dust suspension of powder material and for measuring dustiness characteristics of said powder material dust suspension, comprising:
   means for supplying a material including at least said powder material;
   container means for receiving said material movable from said means for supplying, said container means including an inclined plane disposed within said container means for achieving a pre-selected motion for said material moved from said means for supplying into said container means; and
   means coupled to said container means for measuring said dustiness characteristics of said powder material.

6. An apparatus for generating a dust suspension of powder material and for measuring dustiness characteristics of said powder material dust suspension, comprising:
   means for supplying a material including at least said powder material;
   container means for receiving said material movable from said means for supplying, said container means including diversion means for achieving a pre-selected motion for said material moved from said means for supplying into said container means and said container means further including a measurement chamber portion and a baffle disposed between said measurement chamber portion and said diversion means; and
   means coupled to said container means for measuring said dustiness characteristics of said powder material.

7. An apparatus for generating a dust suspension of powder material and for measuring dustiness characteristics of said powder material dust suspension, comprising:
   means for supplying a material including at least said powder material;
   container means for receiving said material movable from said means for supplying, said container means including diversion means for achieving a pre-selected motion for said material moved from said means for supplying into said container means and said container means further having walls including openings of selected size; and
   means coupled to said container means for measuring said dustiness characteristics of said powder material.

8. An apparatus for generating a dust suspension of powder material and for measuring the propensity to dust of said powder material, comprising;
   means for providing a supply of said powder material;
   container means for receiving said powder material movable from said means for providing, said container means including an inclined ramp for diverting said moved powder material achieving a pre-selected motion for said powder material; and
   means coupled to said container means for measuring the propensity to dust of said powder material.

9. The apparatus as defined in claim 8 wherein said inclined ramp ranges from 45°–70°.

10. The apparatus as defined in claim 8 wherein the dimensions of said container means can be constructed to be of different relative size to adjust said pre-selected motion.

11. The apparatus as defined in claim 8 wherein said container means is open to the atmosphere in one end allowing movement of said dust suspension past said means for measuring.

12. The apparatus as defined in claim 8 further including a baffle for dividing said container means into a diversion chamber portion and a measurement chamber portion.

13. The apparatus as defined in claim 12 wherein the dimensions of said diversion chamber portion, said measurement chamber portion and said baffle can be constructed to be of different relative size for achieving said pre-selected motion.

14. The apparatus as defined in claim 8 wherein said means for providing comprises a container having a trap door for releasing said powder material into said container means.

15. A method for generating a suspension of dust and measuring characteristics of said dust suspension, comprising the steps of:
   providing a supply of material;
   moving said material into container means for receiving and interacting with said material;
   diverting the flow of said moving material using an inclined ramp surface in said containers means, achieving a pre-selected motion for said material and moving said material through a downstream opening out of said container means; and
   measuring said dust suspension characteristics of said material.

16. The method as defined in claim 15 wherein said material undergoes a preliminary step of compacting said material a predetermined amount.

17. The method as defined in claim 15 wherein said step of measuring characteristics comprises at least one of measuring physical characteristics and chemical characteristics and said method further includes the step of changing at least one of said chemical and physical characteristics during the manufacture of said material responsive to the results of said measuring step.

18. A method for generating a suspension of dust and measuring characteristics of said dust suspension, comprising the steps of:
   providing a supply of material;
   moving said material into container means for receiving and interacting with said material;
   diverting the flow of said moving material in said container means before striking the bottom of said container means and generating at least one of a rolling motion and a swirling motion relative to the forward direction of travel of said material; and
   measuring said dust suspension characteristics of said material.

* * * * *